(12) United States Patent
Dobner et al.

(10) Patent No.: US 7,201,759 B2
(45) Date of Patent: Apr. 10, 2007

(54) CERAMIC MICROKERATOME BLADE ASSEMBLY

(75) Inventors: Michael H. Dobner, Honeoye Falls, NY (US); Craig A. Barrile-Josephson, Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 653 days.

(21) Appl. No.: 10/610,001

(22) Filed: Jun. 30, 2003

(65) Prior Publication Data

US 2004/0267296 A1 Dec. 30, 2004

(51) Int. Cl.
*A61F 9/013* (2006.01)
*A61B 17/32* (2006.01)

(52) U.S. Cl. ...................... 606/166; 606/167
(58) Field of Classification Search ............. 606/166, 606/167, 176–178; 30/346
See application file for complete search history.

(56) References Cited

U.S. PATENT DOCUMENTS

| 5,290,301 A * | 3/1994 | Lieberman ............ 606/166 |
| 6,030,398 A | 2/2000 | Klopotek ............ 606/166 |
| 6,099,541 A * | 8/2000 | Klopotek ............ 606/166 |
| 6,447,526 B1 | 9/2002 | Carriazo ............ 606/166 |
| 6,540,760 B2 * | 4/2003 | Austring et al. ............ 606/166 |
| 2001/0014812 A1 | 8/2001 | Dybbs ............ 606/166 |
| 2003/0004526 A1 | 1/2003 | Austring et al. ............ 606/166 |
| 2003/0060840 A1 | 3/2003 | Aufaure et al. ............ 606/166 |
| 2004/0127921 A1 * | 7/2004 | Powell et al. ............ 606/166 |

FOREIGN PATENT DOCUMENTS

WO    WO 02/071990 A2    9/2002

OTHER PUBLICATIONS

Med-Logics, Inc. Web Site Information Product Offering—Calibrated LASIK Blades pp. 3.
Med-Logics, Inc. Web Site Information Design Features and Resulting Benefits pp. 4.
Med-Logics, Inc. Web Site Information Calibrated LASIK Blade Concept Summary pp. 1.

* cited by examiner

*Primary Examiner*—Glenn K. Dawson
*Assistant Examiner*—Kathleen Sonnett

(57) ABSTRACT

A cutting blade assembly 20 includes a ceramic blade 22 with a forward cutting edge 24. A lower portion 28 of a blade holder 26 is formed of ceramic and is integral to ceramic blade 22. An upper blade holder portion 30 is attached to the lower blade holder portion 28, such that the upper blade holder portion 30 is structured for engagement with a microkeratome oscillation mechanism 84.

1 Claim, 2 Drawing Sheets

CERAMIC MICROKERATOME BLADE ASSEMBLY

BACKGROUND OF THE INVENTION

1. Field of the Invention

The present invention relates to blade assemblies for use in microkeratomes. In particular, the present invention is related to a ceramic blade assembly for use in microkeratomes.

2. Description of Related Art

The use of microkeratomes having blades or blade assemblies for use in ophthalmic surgery is well known in the art. Typically, the microkeratome blades and blade assemblies have been fabricated from commercially available razor-blade stock with holders of plastic materials, such as Delrin® attached to the fabricated blade. One such blade assembly is described in U.S. Pat. No. 6,051,009 to Hellenkamp, et al., which patent is herein incorporated in its entirety by reference.

While these metal, razor-blade based assemblies provide precision cuts of corneal tissue, particularly in forming a flap for LASIK (laser-assisted in-situ keratomileusis) surgery, it would be desirable to provide a microkeratome blade assembly that would not require the cleaning and polishing presently required to be performed on the metal blades during manufacture. In addition, it would be desirable to have a blade assembly that provided a very precise blade extension for operating in a microkeratome to provide an extremely precise depth of cut that is repeatable from blade to blade. This extremely precise depth of cut relies on a precise blade extension being provided in the keratome blade designed to be used with a particular microkeratome.

Other blade and blade assembly materials have been suggested in the prior art, such as plastic or ceramic or precious stone materials such as diamonds or sapphires. Examples of such patents suggesting the use of ceramic materials and other materials for microkeratome blade assemblies are U.S. Pat. Nos. 6,030,398 and 6,099,541 issued to Klopotek for surgical microtomes, U.S. Pat. No. 6,447,526 issued to Carriazo for a disposable microkeratome blade housing, and U.S. Pat. No. 6,540,760 issued to Austring, et al. for a cutting blade and cutting blade assembly. While each of these patents suggest using a cutting blade or an entire cutting blade assembly formed of ceramic material, none of the above prior art describes or discloses such a microkeratome blade assembly, let alone a microkeratome blade assembly providing a precise blade extension while also being inexpensive to manufacturer and assemble for use in known microkeratomes such as the Hansatome™ available from Bausch & Lomb Incorporated.

Therefore, it would be desirable to provide a microkeratome blade assembly made of ceramic material that provides an extremely precise blade extension and yet is relatively cheaply and easily manufactured.

DETAILED DESCRIPTION

Figure 1:
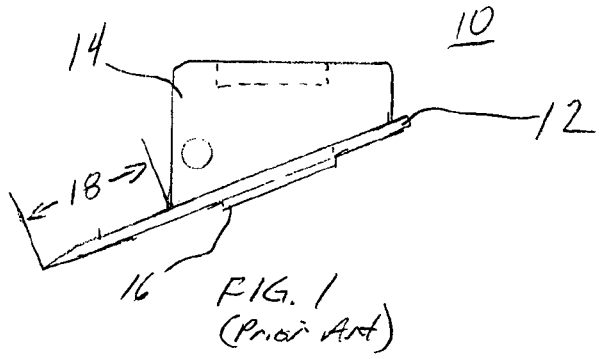
FIG. 1 is a side view of a prior art microkeratome blade assembly.

FIG. 1 shows a side view of a prior art microkeratome blade assembly such as that described in U.S. Pat. No. 6,051,009. The microkeratome blade assembly 10 includes a metal cutting blade 12 which is typically formed from commercially available razor-blade stock, and a blade holder 14 attached to the cutting blade 12. Blade holder 14 is typically formed of a plastic material, such as Delrin® or other suitable plastics. Typically such prior art assemblies had posts 16 extending from blade holder 14 that passed through the blade assembly 12 and are cold or heat staked to the blade assembly 12. Such staking results in a blade extension shown at 18 for blade assembly 10. The blade extension 18 is the major factor in determining the depth of cut in a patient's eye when the blade assembly 10 is used in a microkeratome, such as the Hansatome™ available from Bausch & Lomb Incorporated.

The depth of cut in turn determines a corneal flap thickness that is formed prior to LASIK surgery. The corneal flap thickness is of particular importance to a refractive surgeon, in that a surgeon needs to know the flap thickness in order to determine the amount of corneal tissue available to be ablated by a laser safely, without causing post-operative problems. Attempts have been made in the prior art to control the blade extension 18 such as described in co-pending patent application Ser. No. 10/335,006 by Powell, et al. filed 30 Dec. 2002, and by Medlogics, Inc. as described in published PCT application WO 01/91650 A1 published on 6 Dec. 2001. However, these attempts at blade extension control rely on tolerance stacks of the metal blade and the holes formed in the metal blade in relations to the stakes 16 of the blade holder in conjunction with a fixturing device for assembling the blade onto the blade holder.

The present invention enables a very precise blade extension to be achieved as described below in relation to FIGS. 2–5.

Figure 2:
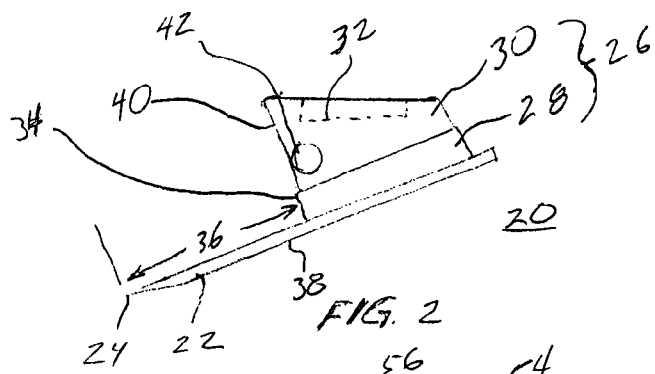
FIG. 2 is a side view of a microkeratome assembly in accordance with the present invention.

FIG. 2 shows a side elevation view of a microkeratome blade assembly in accordance with the present invention 20. Blade assembly 20 preferably includes a ceramic blade 22 with a forward cutting edge 24. Preferably a blade holder 26 is formed by ceramic portion 28 which forms a lower portion of blade holder 26 and is integral to ceramic blade 22 and an upper blade holder portion 30 formed of Delrin® or other suitable materials is attached to the lower blade holder portion 28, such that the upper blade portion is structured for operable engagement with a microkeratome oscillation mechanism (shown at 84 in FIG. 6). The microkeratome oscillation mechanism, typically an eccentric pivoting pin, engages a slot shown as dash line 32 in FIG. 2.

Preferably, blade 22 and lower blade holder portion 28 are formed in a single process, such that lower portion 28 is integral to blade 22, thus forming a monolith. The technology is preferably available from MEMX Incorporated of Albuquerque, N. Mex. In this way, a very precise blade extension can be maintained between the cutting edge 24 and the forward datum surface 34 of lower blade holder portion 28. The blade extension distance is shown at 36. As previously mentioned, this blade extension is the major factor in determining the flap thickness created by the microkeratome prior to LASIK surgery, and thus, the more precisely the blade extension length 36 that can be maintained from blade to blade, the more consistent the flap cuts will be from patient to patient. A bottom surface 38 of blade 22 preferably forms a second datum surface. Preferably, datum surfaces 34 and 38 are urged by a microkeratome against mating surfaces within a cutting head of the microkeratome. In this way, the blade extension 36 used will be precisely the same from blade to blade in that the blade will not be allowed to move away from contact with the microkeratome cutting head. The technology available from MEMX Inc. allows the blade extension distance 36 to be controlled within sub-micro tolerances and therefore, essentially assures that no detectable difference in blade extensions will occur from blade to blade.

Obviously to ensure that datum surface 34 controls the blade extension of the blade assembly within the cutting head assembly, upper blade holder 30 has a forward surface 40 that should be no more forward than surface 34 and actually is preferably slightly behind surface 34 to ensure that datum surface 34 controls the blade extension within the microkeratome cutting head assembly. Cutting blade assembly 20 also preferably includes an access opening 42 for receiving an insertion tool for assisting in the insertion of cutting blade assembly 20 into a microkeratome cutting head assembly.

Preferably, upper blade holder portion 30 is attached to lower blade holder portion 28 by a suitable adhesive and additionally may include structures such as that described below with regard to FIGS. 3 and 4.

Figure 3:
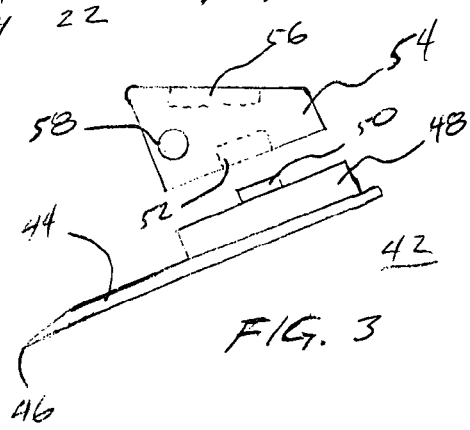
FIG. 3 is an exploded side view of an alternate embodiment in accordance with the present invention.

FIG. 3 shows an alternate embodiment in accordance with the present invention and includes a cutting blade assembly 42 shown in exploded side elevation view. Assembly 42 preferably includes a ceramic blade 44 with a cutting edge 46 and has an integral ceramic lower blade holder portion 48 similar to that described above with regard to FIG. 2. In addition, assembly 42 includes an integral ceramic post 50 which mates with a recess 52 in an upper blade holder portion 54. The advantage of using a post 50 is that it allows upper blade holder portion 54 to be more easily and precisely located on lower blade holder portion 48. The post 50 may be press fit into recess 52 to hold upper blade holder portion 54 onto lower blade holder portion 48 or a combination of press fit and adhesive may be used or only adhesive may be relied on to attach upper blade holder portion 54. In addition, other attachment means may be used such as screws or bolts. Also, such known methods of attachment, such as cold staking and heat staking may be used.

Upper blade holder portion 54 also preferably includes a slot 56 for receiving an oscillation pin of the microkeratome and an insertion tool opening 58 for receiving an insertion tool. It is noted that the cutting bevel of FIG. 3 beginning at cutting edge 46 is in the opposite orientation of that shown in FIG. 2. The orientation that is desired depends on the cutting head assembly and the relation between the leading edges 46 and 24 to the aplanation portion of a cutting head assembly of a microkeratome. Likewise, if a double bevel microkeratome blade were to be incorporated such as that known in the prior art with razor-blade stock, this again would alter the geometry necessary relative to the cutting head assembly required to provide the desired flap thickness.

Figure 4:
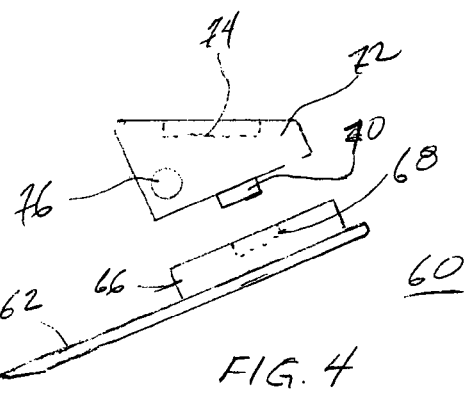
FIG. 4 is an exploded view of yet another alternate embodiment in accordance with the present invention.

FIG. 4 shows still another alternate embodiment in accordance with the present invention, wherein a ceramic blade assembly 60 includes a ceramic blade 62 having a cutting edge 64 and a lower integral ceramic blade holder portion 66. In the embodiment of FIG. 4, lower ceramic blade holder portion 66 includes a recess 68 for receiving a post 70 of upper blade holder portion 72. Again as described above several means of attaching upper blade holder portion 72 to lower blade holder portion 68 may be utilized. As before, upper blade holder portion 72 preferably includes oscillation pin slot 74 and insertion tool access 76.

Figure 5:
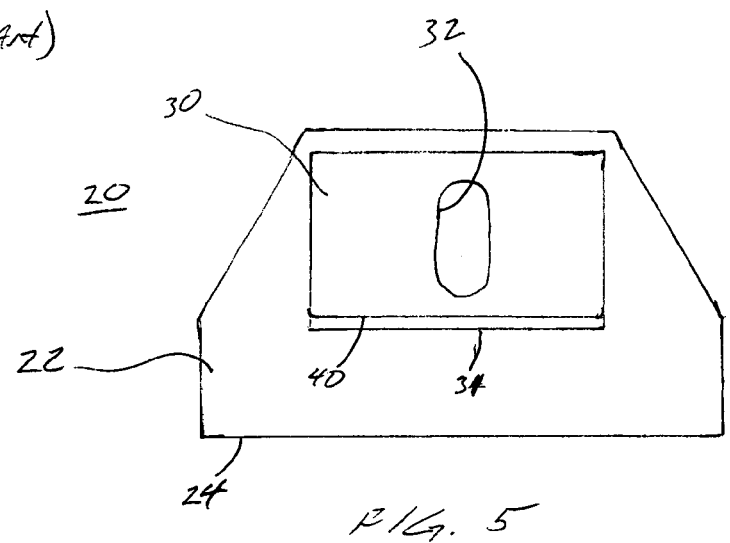
FIG. 5 is a top view of a microkeratome blade assembly in accordance with the present invention.

FIG. 5 shows an upper view of cutting blade assembly 20. As shown, it is preferred that forward datum surface 34 is forward of upper blade holder portion forward surface 40. The upper blade holder portion 30 is shown to be co-extensive with the footprint of lower blade holder portion 28, but could be made to extend beyond the sides of and to the rear of blade holder portion 28. However, it is important that in order to maintain precise blade extension as described above, that datum surface 34 be the leading edge of the cutting blade assembly 20 that surface 34 contacts a mating surface in the cutting head assembly of a microkeratome.

The cutting blade assemblies shown and described above, are for use with a pivoting microkeratome, such as the Hansatome available from Bausch & Lomb Incorporated. However, other blade assemblies of other geometric configurations could be also made, such as for a linear microkeratome that would still benefit from the precise blade extension provided by the current invention.

Forming the entire blade holder 26 of ceramic would be very difficult if not impossible and would greatly increase the expense of manufacturing a cutting blade assembly. This is because of the angles which would need to be formed in the ceramic are difficult to produce.

Figure 6:
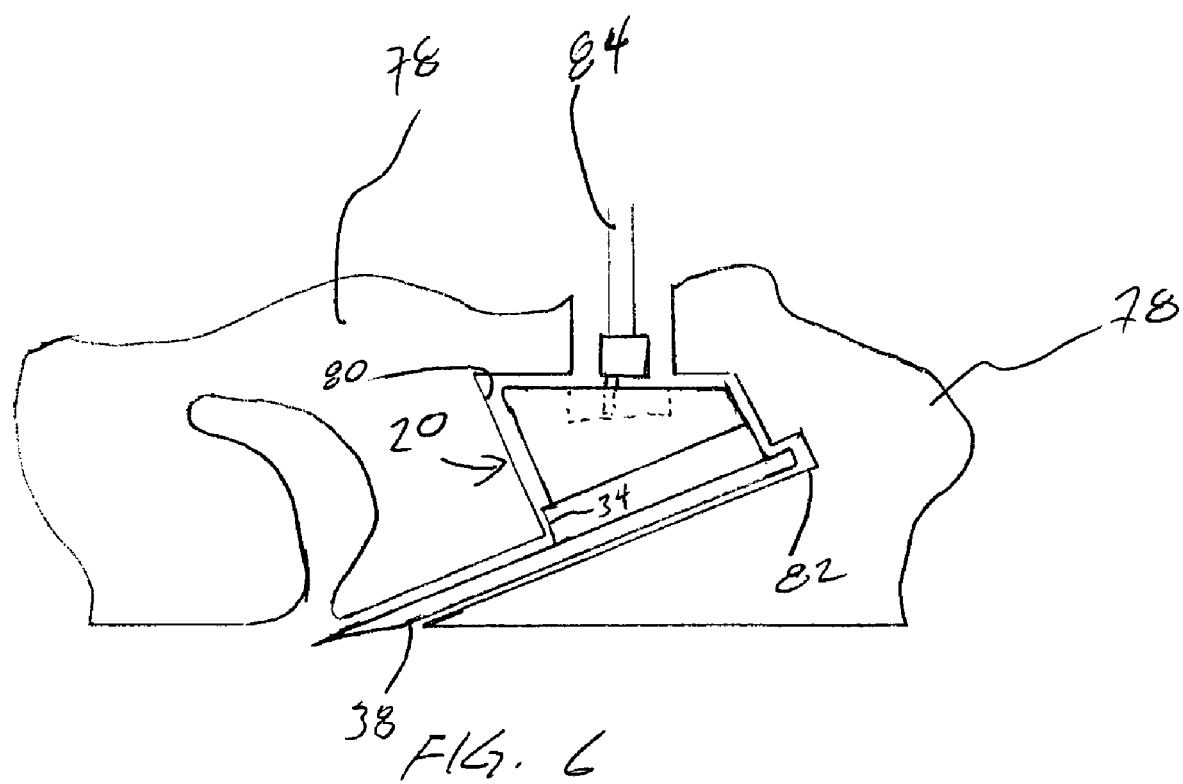
FIG. 6 is a partial view of a cutting head assembly with a cutting blade assembly in accordance with the present invention held within a cutting head assembly.

FIG. 6 shows a partial view of a cutting head assembly 78 containing cutting blade assembly 20 as can be seen from FIG. 6 datum surfaces 34 and 38 abutt mating surfaces 80 and 82 in the cutting head assembly 78 when oscillation pin 84 exerts force downwardly against cutting blade assembly 20. In this manner, precise blade extension is maintained during use of cutting blade assembly in cutting head assembly 78.

We claim:

1. A cutting blade assembly for use in a microkeratome comprising:

a ceramic blade including a forward cutting edge;

a lower portion of a blade holder formed of ceramic and together with the ceramic blade forming a monolith, the lower blade holder portion including a forward datum surface;

an upper blade holder portion attached to the lower blade holder portion including a forward surface at a distance from the cutting edge that is equal to or greater than a distance from the cutting edge to the forward datum surface of the lower blade holder portion; and wherein a forward surface of the lower blade holder portion and a bottom surface of the ceramic blade are datum surfaces for abutting mating structure in a microkeratome cutting head assembly for achieving precise blade extension during use of the microkeratome.

* * * * *